US010321892B2

United States Patent
Wang et al.

(10) Patent No.: US 10,321,892 B2
(45) Date of Patent: Jun. 18, 2019

(54) COMPUTERIZED CHARACTERIZATION OF CARDIAC MOTION IN MEDICAL DIAGNOSTIC ULTRASOUND

(75) Inventors: Yang Wang, Plainsboro, NJ (US); Bogdan Georgescu, Plainsboro, NJ (US); Helene C. Houle, San Jose, CA (US); Dorin Comaniciu, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 551 days.

(21) Appl. No.: 13/234,697

(22) Filed: Sep. 16, 2011

(65) Prior Publication Data

US 2012/0078097 A1 Mar. 29, 2012

Related U.S. Application Data

(60) Provisional application No. 61/482,714, filed on May 5, 2011, provisional application No. 61/386,642, filed on Sep. 27, 2010.

(51) Int. Cl.
*A61B 8/00* (2006.01)
*A61B 8/08* (2006.01)
*G06T 7/246* (2017.01)

(52) U.S. Cl.
CPC .......... *A61B 8/483* (2013.01); *A61B 8/0883* (2013.01); *G06T 7/251* (2017.01); *A61B 8/00* (2013.01);
(Continued)

(58) Field of Classification Search
CPC ......... A61B 8/085; A61B 8/483; G06T 7/251; G06T 2207/10136; G06T 2207/30048
(Continued)

(56) References Cited

U.S. PATENT DOCUMENTS 5,265,035 A * 11/1993 Reifman et al. ............... 702/185
5,776,063 A * 7/1998 Dittrich ................. A61B 8/481
600/408

(Continued)

FOREIGN PATENT DOCUMENTS

| WO | WO 2007058997 A2 * | 5/2007 |
| WO | WO 2008018029 A1 * | 2/2008 |
| WO | WO 2009057035 A1 * | 5/2009 |

OTHER PUBLICATIONS

L Yang, B Georgescu, Y Zheng, DJ Foran, D Comaniciu, "A Fast and Accurate Tracking Algorithm of Left Ventricles in 3D Echocardiography", 2008, Proc. IEEE Int Symp Biomend Imaging, May 14, vol. 5, pp. 221-224.*

(Continued)

*Primary Examiner* — James M Kish

(57) ABSTRACT

Computerized characterization of cardiac wall motion is provided. Quantities for cardiac wall motion are determined from a four-dimensional (i.e., 3D+time) sequence of ultrasound data. A processor automatically processes the volume data to locate the cardiac wall through the sequence and calculate the quantity from the cardiac wall position or motion. Various machine learning is used for locating and tracking the cardiac wall, such as using a motion prior learned from training data for initially locating the cardiac wall and the motion prior, speckle tracking, boundary detection, and mass conservation cues for tracking with another machine learned classifier. Where the sequence extends over multiple cycles, the cycles are automatically divided for independent tracking of the cardiac wall. The cardiac wall from one cycle may be used to propagate to another cycle for initializing the tracking. Independent tracking in each cycle may reduce or avoid inaccuracies due to drift.

18 Claims, 6 Drawing Sheets

(52) U.S. Cl.
CPC ............... *G06T 2207/10136* (2013.01); *G06T 2207/30048* (2013.01)

(58) Field of Classification Search
USPC ........................................................ 600/437
See application file for complete search history.

(56) References Cited

U.S. PATENT DOCUMENTS

| | | | |
|---|---|---|---|
| 5,797,396 A * | 8/1998 | Geiser ...................... | G06T 7/66 382/128 |
| 6,103,350 A * | 8/2000 | Grangeat et al. .......... | 428/195.1 |
| 6,628,743 B1 * | 9/2003 | Drummond et al. ............. | 378/8 |
| 7,333,850 B2 * | 2/2008 | Marossero et al. ........... | 600/511 |
| 7,366,053 B2 * | 4/2008 | Audi et al. ...................... | 367/11 |
| 7,565,276 B2 * | 7/2009 | Song et al. ........................ | 703/2 |
| 7,889,898 B2 | 2/2011 | Chakraborty et al. | |
| 2004/0208341 A1 * | 10/2004 | Zhou ..................... | G06K 9/3216 382/103 |
| 2004/0249281 A1 * | 12/2004 | Olstad ............................. | 600/437 |
| 2005/0033179 A1 * | 2/2005 | Gardner et al. .............. | 600/458 |
| 2005/0059876 A1 | 3/2005 | Krishnan et al. | |
| 2006/0064007 A1 * | 3/2006 | Comaniciu ............. | A61B 8/463 600/416 |
| 2006/0074315 A1 * | 4/2006 | Liang ....................... | A61B 8/02 600/450 |
| 2006/0079781 A1 * | 4/2006 | Germond-Rouet et al. ................... | 600/450 |
| 2006/0111877 A1 * | 5/2006 | Haselhoff .............. | A61B 5/055 702/193 |
| 2006/0171586 A1 * | 8/2006 | Georgescu ........... | G06K 9/6255 382/128 |
| 2006/0247544 A1 * | 11/2006 | Qazi et al. ..................... | 600/508 |
| 2007/0116339 A1 * | 5/2007 | Shen .............................. | 382/128 |
| 2007/0239000 A1 * | 10/2007 | Emery et al. ................. | 600/437 |
| 2008/0009722 A1 * | 1/2008 | Simopoulos ............. | A61B 8/08 600/437 |
| 2008/0015428 A1 * | 1/2008 | Epstein .................... | G06T 7/215 600/410 |
| 2008/0101676 A1 * | 5/2008 | Zheng et al. ................. | 382/131 |
| 2008/0249414 A1 * | 10/2008 | Yang .................... | A61B 8/0883 600/445 |
| 2009/0074280 A1 * | 3/2009 | Lu et al. ....................... | 382/131 |
| 2009/0093717 A1 | 4/2009 | Carneiro et al. | |
| 2009/0096807 A1 * | 4/2009 | Silverstein et al. .......... | 345/593 |
| 2009/0131788 A1 * | 5/2009 | Settlemier ............ | A61B 8/0858 600/438 |
| 2010/0041992 A1 | 2/2010 | Ohuchi et al. | |
| 2010/0189317 A1 * | 7/2010 | Lehmann ............... | A61B 6/463 382/128 |
| 2010/0198072 A1 | 8/2010 | Abe et al. | |
| 2010/0268059 A1 * | 10/2010 | Ryu ....................... | A61B 5/042 600/407 |
| 2011/0243401 A1 * | 10/2011 | Zabair ..................... | G06K 9/00 382/128 |

OTHER PUBLICATIONS

L Yang, B Georgescu, Y Zheng, DJ Foran, D Comaniciu, "A Fast and Accurate Tracking Algorithm of Left Ventricles in 3D Echocardiography", May 14, 2008, Proc IEEE Int Symp Biomed Imaging, vol. 5, pp. 221-224.*

J Jiang, TJ Hall, "A Generalized Speckle Tracking Algorithm for Ultrasonic Strain Imaging Using Dynamic Programming", 2009, Ultrasound in Med. & Biol., vol. 35, No. 11, pp. 1863-1879.*

Y. Wang et al., "Learning-Based 3D Myocardial Motion Flow Estimation Using High Frame Rate Volumetric Ultrasound Data," Apr. 14, 2010.

Y. Zheng et al., "Fast Automatic Heart Chamber Segmentation from 3D CT Data Using Marginal Space Learning and Steerable Features," IEEE, 2007.

Z. Tu, "Probabilistic Boosting-Tree: Learning Discriminative Models for Classification, Recognition, and Clustering," In ICCV, pp. 1589-1596, 2005.

J. D'hooge et al., "Regional Strain and Strain Rate Measurements by Cardiac Ultrasound: Principles, Implementation and Limitations," Eur. J. Echocardiography, vol. 1, Issue 3, pp. 154-170, Sep. 2000.

K. Kaluzynski et al., "Strain Rate Imaging Using Two-Dimensional Speckle Tracking," IEEE Transactions on Ultrasonics, Ferroelectrics and Frequency Control, vol. 48, No. 4, pp. 111-1123, Jul. 2001.

M. Suffoletto et al., "Novel Speckle-Tracking Radial Strain From Routine Black-and-White Echocardiographic Images to Quantify Dyssynchrony and Predict Response to Cardiac Resynchronization Therapy," Journal of the American Heart Association, Circulation 113, pp. 960-968, Feb. 2006.

M. Ledesma-Carbayo et al., "Spatio-Temporal Nonrigid Registration for Ultrasound Cardiac Motion Estimation," IEEE Transactions on Medical Imaging, vol. 24, No. 9, pp. 1113-1126, Sep. 2005.

F. C.P. Yin et al., "Compressibility of Perfused Passive Myocardium," American Journal of Physiology, vol. 271, No. 5, pp. 1864-1870, Apr. 1996.

Y. Zhu et al., "Cardiac MR Image Segmentation with Incompressibility Constraint," In ISBI, pp. 185-188, 2007.

B. J. Krenning et al., "Assessment of Left Ventricular Function by Three-Dimensional Echocardiography," Cardiovascular Ultrasound, 1:12, pp. 1-7, Sep. 2003.

L. Xioaguang et al., "AUTOMPR: Automatic Detection of Standard Planes in 3D Echocardiography," In ISBI, pp. 1279-1282, 2008.

Y. Zheng et al., "Four-Chamber Heart Modeling and Automatic Segmentation of 3-D Cardiac CT Volumes Using Marginal Space Learning and Steerable Features," IEEE Transactions on Medical Imaging, vol. 27, No. 11, pp. 1668-1681, 2008.

A. Elen et al., "Three-Dimensional Cardiac Strain Estimation Using Spatio-Temporal Elastic Registration of Ultrasound Images: A Feasibility Study," IEEE Transactions on Medical Imaging, vol. 27, No. 11, pp. 1580-1591, Nov. 2008.

Q. Duan et al., "Validation of Optical-Flow for Quantification of Myocardial Deformations on Simulated RT3D Ultrasound," IEEE Int'l Sym. Biomedical Imaging, pp. 944-947, 2007.

H. Feigenbaum et al., "Feigenbaums Echocardiography," Lippincott Williams &Wilkins, 2005.

L. Yang et al. "3D ultrasound tracking of the left ventricles using one-step forward prediction and data fusion of collaborative trackers," CVPR (2008).

J.B. Tenenbaum et al. "A global geometric framework for nonlinear dimensionality reduction," Science 290(5500) (2000) 2319-2323.

European Search Report dated Apr. 8, 2013.

Office Action dated Oct. 6, 2015 in corresponding European Application No. 11182366.2.

* cited by examiner

US 10,321,892 B2

COMPUTERIZED CHARACTERIZATION OF CARDIAC MOTION IN MEDICAL DIAGNOSTIC ULTRASOUND

RELATED APPLICATIONS

The present patent document claims the benefit of the filing date under 35 U.S.C. § 119(e) of Provisional U.S. Patent Application Ser. Nos. 61/482,714, filed May 5, 2011, and 61/386,642, filed Sep. 27, 2010, which are hereby incorporated by reference.

BACKGROUND

This present invention relates to characterizing cardiac motion from ultrasound information.

Being a non-invasive and cost effective modality, ultrasound is usually the initial method to quantify cardiac mechanics in a non-invasive manner. Recent developments in the field of echocardiography allow the cardiologist to quantify cardiac strain in a non-invasive manner. However, most existing methods for measuring myocardial strain are limited to measurements in one or two dimensions.

The myocardium changes during a cardiac cycle. The volume of the ventricular wall itself may remain relatively consistent during the cardiac cycle, such with a change less than 5%. Since myocardial tissue is virtually incompressible, the tissue deforms in all three dimensions simultaneously. Therefore, it is important to compute the cardiac motion in three-dimensions.

Given the recent progress on real-time ultrasound imaging, unstitched volumetric data can be captured in a high volume rate, which allows quantification of cardiac strain and other parameters in three-dimensions. For example, the estimation and analysis of cardiac motion provides important information for the elasticity and contractility of the myocardium. Although visual wall motion scoring is the clinically established method for assessment of regional myocardial function, this methodology may be variable between observers. To quantify from a sequence of volumes (e.g., 3D+t or 4D), manual tracing becomes burdensome.

BRIEF SUMMARY

By way of introduction, the preferred embodiments described below include methods, computer readable media and systems for computerized characterization of cardiac wall motion. Quantities for cardiac wall motion are determined from a four-dimensional (i.e., 3D+time) sequence of ultrasound data. The quantities are determined with minimal user input. A processor automatically processes the volume data to locate the cardiac wall through the sequence and calculate the quantity from the cardiac wall position or motion. Various machine learning is used for locating and tracking the cardiac wall, such as using a motion prior learned from training data for locating and the motion prior, speckle tracking, boundary detection, and mass conservation cues for tracking with another machine learned classifier.

Where the sequence extends over multiple cycles, the cycles are automatically divided for independent tracking of the cardiac wall. Independent tracking in each cycle may reduce or avoid inaccuracies due to drift. The cardiac wall from one cycle may be used to propagate to another cycle for initializing the independent tracking. The tracked cardiac wall from a plurality of cycles may be fused temporally to enhance tracking accuracy and robustness.

In a first aspect, a method is provided for computerized characterization of cardiac motion from ultrasound data. A sequence of frames of ultrasound data is obtained. The frames represent a volume of a patient at different times. A processor identifies a myocardium in a first frame. The processor estimates non-rigid deformation of a myocardium through the sequence where the estimating is a function of a machine-learned model of the intensity, speckle patterns, or intensity and speckle patterns specific to the left ventricle myocardium using discriminative classifiers. The machine-learned model is a motion prior. The estimating is also a function of volumetric tracking of the myocardium from the first frame to a second frame of the sequence of the frames. The processor calculates a first myocardial mechanical quantity as a function of the non-rigid deformation. The quantity is projected to a Cartesian coordinate system and a local heart coordinate system.

In a second aspect, an automatic semantic processing framework is provided for estimation of volume myocardial mechanics. Tracing and tracking are integrated using specific knowledge of the anatomy involved for full myocardial mechanics computation from 3d+t volumetric ultrasound images. A fully automatic system is provided with information fusion-based robust tracking and comprehensive parameter estimation of myocardium mechanics. The automated system includes automatic initialization of myocardial boundaries and multi-planar reconstruction (MPR) planes in the first frame by real-time detection. Automatic tracking of the myocardium motion and estimation of clinical cardiac parameters in three-dimensional space is provided. Information from multiple cues, such as speckle tracking, boundary detection, mass conservation, and/or motion prior, are fused into a single Bayesian objective function to achieve accurate and robust tracking of the whole myocardium volume.

In a third aspect, a non-transitory computer readable storage media has stored therein data representing instructions executable by a programmed processor for characterizing cardiac motion from ultrasound information. The storage media includes instructions for obtaining a sequence of frames of ultrasound data, the frames representing a volume of a patient at a different times, identifying first and second cycles of the heart from the sequence of the frames of the ultrasound data, and propagating a first location of a myocardium from a first frame of the frames of the first cycle to a second location of the myocardium in a second frame of the frames of the second cycle, the second location being an initial location of the myocardium used in volumetric tracking of the myocardium through the frames of the second cycle.

In a fourth aspect, a non-transitory computer readable storage media has stored therein data representing instructions executable by a programmed processor for characterizing cardiac motion from ultrasound information in an automatic manner. The storage media includes instructions for locating a heart wall from a first frame of ultrasound data in a sequence representing the heart wall in three dimensions, the locating being a function of a first machine-learned knowledge of the heart wall represented in training data, tracking the heart wall automatically through the sequence, the tracking being a function of a second machine-learned knowledge of a plurality of cues, the plurality of cues including the first machine-learned knowledge with speckle tracking, boundary detection, mass conservation, a motion prior, and calculating a cardiac parameter, statistical index of the cardiac motion, or both the cardiac parameter and the statistical index of the cardiac motion as a function of the tracking.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
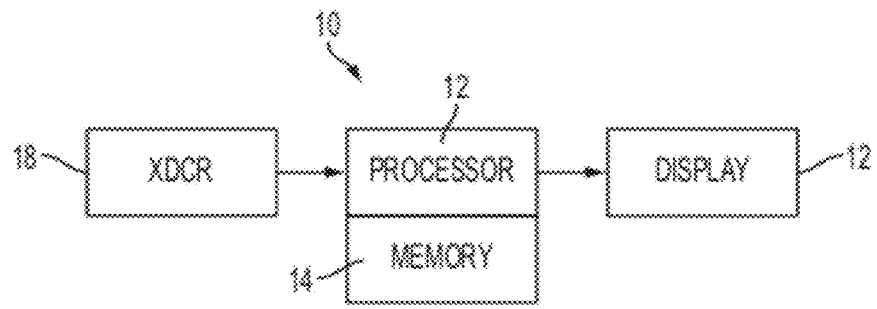
FIG. 1 is a block diagram of one embodiment of a system for characterizing cardiac motion from ultrasound information.

To quantitatively detect wall-motion abnormalities of the left ventricle (LV), automated analysis of LV wall motion may be preferred to visual assessments. Cardiac motion is quantified by recovering the three-dimensional (3D) non-rigid deformation of the ventricular wall from 3D+t ultrasound images or frames of data. Robust multi-cycle ventricular wall motion tracking on volumetric ultrasound data is provided. By using knowledge-based 3D+t myocardial function assessment, automated cardiac quantification is provided. Myocardial mechanics, such as an atlas based representation, are determined with a multi-model, learning-based motion estimation using high frame rate volumetric ultrasound data.

Given the recent progress on real-time ultrasound imaging, high frame rate volumetric ultrasound images or frames of data may be acquired over multiple cardiac cycles. Detecting motion in three-dimensions may be more useful than the more arbitrary motion detection in one or more planes. The estimation and analysis of cardiac motion may provide important information for the quantification of the elasticity and contractility of the myocardium. Detecting motion over multiple cycles may be more useful than over a single cycle, especially where drift in tracking is avoided.

Multiple types of information, such as image gradients, boundary detection and motion prediction, are fused to achieve a robust tracking on 3D+t ultrasound sequences. The use of these types of information may allow efficient, high speed performance, such as tracking at 1 second per frame for volumetric ultrasound data on a 3.0 GHz personal computer (PC) machine.

Detection of wall-motion abnormalities of the left ventricle (LV) provides important information on myocardial (dys-)function in a variety of clinical settings, and is widely accepted as a predictor for non-ischemic cardiomyopathy and coronary artery disease. Boosted by automatic detection and tracking techniques, 3D non-rigid deformation of the myocardium may be recovered from 3D+t ultrasound data, allowing for statistical atlases of cardiac motion on a large population. Normal and diseased myocardial motion patterns may be automatically detected, and the severity of a disease determined using the statistical atlases of myocardial deformation parameters based on statistical indices, such as Hotelling's t-square score, to measure the deviation from healthy cardiac motion patterns. A learning-based method automatically estimates the 3D displacements and velocities of the myocardial motion.

In one embodiment, a fully automatic method and system estimates the 3D non-rigid deformation of the whole myocardium on instantaneous volumetric ultrasound data using database-guided detection and information fusion-based tracking. Global and regional myocardial mechanics are estimated based on the tracking result. The quantified mechanics may include parameters such as volume, velocity, displacement, twist, torsion, strain, strain rate, principal strain, radius, curvature, contraction front mapping (CFM), relaxation front mapping (RFM), and Coronary Map. The mechanics may be reported in graphical, parametric, chart, numerical, and/or bull's eye representations. The parameters may be projected to the local heart coordinate system (e.g., the longitudinal (meridional) DL, radial (transmural) DR, and circumferential DC directions).

Quantified mechanics parameters may be fused with other imaging modalities, such as coronary CT (Computed Tomography) data, to enhance visualization quality and diagnostic confidence of physicians.

While discussed herein for use on the myocardium or left ventricle with ultrasound data, the approach may be considered a general framework. This general framework may be applied to other portions of the heart and/or other organs. The general framework may be applied to other imaging modalities, such as x-ray, computed tomography, or magnetic resonance imaging. The systems, methods and instructions herein may instead or additionally be used for other cyclical or repetitive motion characterization, such as analysis of diaphragm motion or a gait while jogging. In yet other embodiments, non-medical analysis is performed using the methods, systems, or instructions disclosed herein, such as analysis of turbine blade vibrations or structural reaction to environmental conditions (e.g., bridge variation due to wind). The medical imaging cardiac example is used herein.

Automatic semantic processing provides myocardial mechanics. Tracing and tracking are integrated using specific knowledge of the anatomy involved for full myocardial mechanics computation from 3d+t volumetric ultrasound images. A fully automatic system is provided with information fusion-based robust tracking and comprehensive parameter estimation of myocardium mechanics. The automated system includes automatic initialization of myocardial boundaries and multi-planar reconstruction (MPR) planes in the first frame by real-time detection. Automatic tracking of the myocardium motion and estimation of clinical cardiac parameters in three-dimensional space is provided. Information from multiple cues, such as speckle tracking, boundary detection, mass conservation, and/or motion prior, are fused into a single Bayesian objective function to achieve accurate and robust tracking of the whole myocardium volume. Efficient optimization, such as manifold learning, is used to achieve high speed.

Automatic temporal adjustment is provided for when ECG is not available or not correct. Boundary detection and motion prediction are combined with image intensity to prevent drifting in multiple cardiac cycles.

In one embodiment, the process proceeds through a number of actions. In a first action, automatic temporal segmentation is provided. When ECG information is not available or not correct, pre-processing automatically estimates one or more key frames (e.g., end diastole (ED) and/or end systole (ES)).

In a second action, automatic data navigation is provided. To be compatible with two-dimensional (2D) analysis, standard multi-planar reformatted planes (MPRs) (e.g., apical four chamber, apical two chamber, apical three chamber, and short axis views) are extracted from the 3D volumetric data automatically.

In a third action, automatic tracking initialization is provided. The initial endocardial and epicardial boundaries of the left ventricle (LV) are obtained using a marginal space learning (MSL) classifier. Other classifiers may be used.

In a fourth action, ventricular wall motion tracking is provided. The 3D deformation of the myocardial wall is captured by fusing the information from multiple cues, including speckle tracking, boundary detection and motion prior.

This framework may have advantages as compared to mere image registration or optical flow tracking. Boundary detection and motion prediction are combined with image intensity information to prevent drifting. The improved tracking accuracy and robustness may better track ventricular wall motion reliably in multiple cardiac cycles. Efficient optimization may achieve high speed performance. Initialization (e.g., location of the endocardial wall in one frame) is automatic. Automatic temporal segmentation may be used to report the number of heart beats, the number of frames in each beat, and the indices of end-diastolic (ED) and end-systolic (ES) frames.

FIG. 1 shows a system 10 for characterizing cardiac motion. The system 10 includes a processor 12, a memory 14, a transducer 18, and a display 16. Additional, different or fewer components may be provided. In one embodiment, the system 10 is a medical diagnostic imaging system, such as an ultrasound imaging system. As or after frames of data representing a patient's heart in three-dimensions are acquired, the system 10 automatically characterizes the cardiac motion of the heart. As an ultrasound imaging system, the system 10 includes a transmit beamformer, receive beamformer, B-mode detector, Doppler detector, harmonic response detector, contrast agent detector, scan converter, filter, combinations thereof, or other now known or later developed medical diagnostic ultrasound system components. In other embodiments, the system 10 is a computer, workstation or server. For example, a local or remote workstation without the transducer 18 receives ultrasound data and characterizes cardiac motion.

The transducer 18 is a piezoelectric or capacitive device operable to convert between acoustic and electrical energy. The transducer 18 is an array of elements, such as a multi-dimensional or two-dimensional array. Alternatively, the transducer 18 is a wobbler for mechanical scanning in one dimension and electrical scanning in another dimension.

The system 10 uses the transducer 18 to scan a volume. Electrical and/or mechanical steering allows transmission and reception along different scan lines in the volume. Any scan pattern may be used. In one embodiment, the transmit beam is wide enough for reception along a plurality of scan lines. In another embodiment, a plane, collimated or diverging transmit waveform is provided for reception along a plurality, large number, or all scan lines.

Ultrasound data representing a volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data may be of any type, such as B-mode, flow mode, Doppler mode, contrast agent, harmonic, or other ultrasound modes of imaging.

The ultrasound data is grouped into frames. Each frame includes the ultrasound data sufficient to detect values for the voxels representing the volume of the patient. For B-mode, the ultrasound data includes samples from the receive scan lines. The ultrasound data is beamformed or detected. For Doppler, the ultrasound data may include samples from a plurality of reception events performed along each scan line or estimated velocity or energy samples for each scan line. Each frame of data represents the volume at a given time. Different frames represent substantially the same volume at different times. Substantially accounts for unintended patient or sonographer movement and/or movement caused by the heart cycle.

The processor 12 is one or more general processors, digital signal processors, application specific integrated circuits, field programmable gate arrays, servers, networks, digital circuits, analog circuits, combinations thereof, or other now known or later developed device for processing medical ultrasound data. The processor 12 implements a software program, such as code generated manually or programmed or a trained classification system. For example, the processor 12 is a classifier implementing a graphical model (e.g., Bayesian network, factor graphs, or hidden Markov models), a boosting base model, a decision tree, a neural network, combinations thereof or other now known or later developed algorithm or training classifier. The classifier is configured or trained for distinguishing between the desired groups of states or to identify options and associated probabilities. The processor 12 may implement multiple classifiers with or without further programming to identify the left ventricle, track motion of the heart, and/or calculate parameters.

The processor 12 performs machine learning and/or applies a machine-learned algorithm. For example, the processor 12 applies a probabilistic model to detect the myocardium and/or to track the myocardium. The probabilistic model is a machine-learned classifier. Any classifier may be applied, such as a model-based classifier or a learned classifier (e.g., classifier based on machine learning). For learned classifiers, binary or multi-class classifiers may be used, such as Bayesian or neural network classifiers. In one embodiment, a binary boosting classifier with a tree and cascade structure is used. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used. The classifier is instructions, a matrix, a learned code, or other software and/or hardware for distinguishing between information in frames of ultrasound data.

The classifier may include a plurality of models or classifiers (e.g., detectors) operable together or independently. For example, different probabilistic models are trained, such as one for detecting the myocardium in a given frame of ultrasound data and another for tracking the myocardium between frames. The tracking model may use the output of the detection model. The probabilistic models may be joint or dependent.

For application, the processor 12 calculates features for classification. The same or different features are used for classification in each stage. For example, features are calculated for each frame of data from the data itself for detecting the myocardium. Other features, such as the output of the detection, features from the data itself, and/or other types of information in a fusion for tracking, are calculated for tracking. Using a machine-trained translation classifier, the features are used to rule out hypotheses and/or select a hypothesis corresponding to the location of the myocardium.

In one embodiment for detection and/or tracking, the features are three-dimensional features. 3D data is used to calculate the features. The window function defining the data is a cube, but may have other volume shapes. The window is translated, rotated, and scaled as part of searching for an anatomy. The same or different sized windows are used for different anatomies.

Any features may be used. Different types of features may be used for the same classifier, or all of the features are of a same type for a given classifier. In one embodiment, Haar wavelet-like and/or steerable features are calculated. The features represent directional gradients. Haar wavelet-like features represent the difference between different portions of a region. Any number of features may be used, such as tens, hundreds, or thousands. The machine learning process may operate to determine a desired subset or set of features to be used for a given classification task. In one embodiment, the type of features used is gradient features. For example, the "steerable" features described by Zheng, et al. in "Fast Automatic Heart Chamber Segmentation from 3D CT Data Using Marginal Space Learning and Steerable Features," Proc. Int'l Conf. on Computer Vision, pp. 1-8, 2007, are used. Other types of features may alternatively or additionally be used.

The ultrasound data may be processed prior to calculating features. For example, the gradients throughout the frame are calculated. The features are determined from the gradient information. As another example, low, high, or bandpass filtering is applied.

The classifier is trained from a training data set using a computer. Any number of expert annotated sets of ultrasound data is used. For example, about 200 hundred ultrasound sequences representing the whole or at least a majority of the myocardium are annotated. The annotation is a line, points, curves or volumes (e.g., a mesh or surface) associated with myocardium boundary. The annotation is provided for each frame of data. This large number of annotations allows use of a probabilistic boosting tree to learn relevant features over a large pool of 3D Haar features and/or steerable features. Both features may be efficiently computed and be effective as a feature space for boosting classifiers. Other features may be used. Each classifier uses the data sets and annotations specific to the anatomy being classified.

In one embodiment, the classifier is a knowledge-based probabilistic model, such as marginal space learning using a hierarchical search. A database of known cases is collected for machine learning, providing a database-driven knowledge-based approach. For training data, three-dimensional context information is preserved and guides the detection process. Knowledge is embedded in large annotated data repositories where expert clinicians manually indicate the anatomies. The known cases may be spatially aligned or registered, such as by aligning the coordinate system to the heart. The detected boundary may be scaled and/or aligned to a model or otherwise normalized. The detectors are trained on a large number of annotated 3D ultrasound volumes. The classifier learns various feature vectors for distinguishing between a desired anatomy and information not being detected. In alternative embodiments, the classifier is manually programmed.

The probabilistic boosting tree (PBT) unifies classification, recognition, and clustering into one treatment. For example, the detection and/or tracking classifiers are trained as a probabilistic boosting tree. The classifier is a tree-based structure with which the posterior probabilities of the presence of the anatomy of interest are calculated from given data. Each detector not only provides a binary decision for a given sample, but also a confidence value associated with the decision. The nodes in the tree are constructed by a combination of simple classifiers using boosting techniques, such as disclosed by Tu, "Probabilistic Boosting-Tree: Learning Discriminative Models for Classification, Recognition, and Clustering," Proc. Int'l Conf. on Computer Vision, pp 1589-1596, 2005.

The classifier is trained and applied as a machine-trained marginal space detection and/or fused information tracking classifier. The resulting machine-trained classifiers are applied as a detector of the myocardium in a given frame and tracking the myocardium between frames.

The processor 12 is operable to calculate cardiac related information, such as calculating area, volume, identifying cardiac cycle time periods, determining spatial parameter values as a function of time, strain, elasticity, twist, torsion, and/or characterize cardiac motion. In one embodiment, the processor 12 implements a model or trained classification system (i.e., the processor is a classifier) programmed with desired thresholds, filters or other indicators of class. For example, the processor 12 or another processor tracks one or more points and calculates spatial parameter values for each point in a model. For example, the characterization processes, systems or instructions used in U.S. Patent Publication No. 2005-0059876, the disclosure of which is incorporated herein by reference, are used. One method is described which characterizes the motion of each segment of the heart on a scale of 1-5, as per guidelines from the American Society of Echocardiography. The classification may be performed using the motion information described above.

The memory 14 is a non-transitory computer readable storage media. Computer readable storage media include various types of volatile and non-volatile storage media, including but not limited to random access memory, read-only memory, programmable read-only memory, electrically programmable read-only memory, electrically erasable read-only memory, flash memory, magnetic tape or disk, optical media and the like.

The memory 14 stores the ultrasound frame or image data. The data is stored for or during processing by the processor 12. For example, ultrasound data is a sequence of B-mode images or frames representing a myocardium at different times. The sequences are in a clip stored in a CINE loop, DICOM images or other format. The ultrasound data is input to the processor 12 or the memory 14.

The memory 14 may store data representing instructions executable by a programmed processor, such as the processor 12, for characterizing cardiac motion from ultrasound information. The automatic or semiautomatic operations discussed herein are implemented, at least in part, by the instructions. In one embodiment, the instructions are stored on a removable media drive for reading by a medical diagnostic imaging system or a workstation networked with imaging systems. An imaging system or work station uploads the instructions. In another embodiment, the instructions are stored in a remote location for transfer through a computer network or over telephone communications to the imaging system or workstation. In yet other embodiments, the instructions are stored within the imaging system on a hard drive, random access memory, cache memory, buffer, removable media or other device.

The instructions are for characterizing cardiac motion from ultrasound information. The functions, acts or tasks illustrated in the figures or described herein are performed by the programmed processor 12 executing the instructions stored in the memory 14 or a different memory. The functions, acts or tasks are independent of the particular type of instructions set, storage media, processor or processing strategy and may be performed by software, hardware, integrated circuits, film-ware, micro-code and the like, operating alone or in combination. Likewise, processing strategies may include multiprocessing, multitasking, parallel processing and the like.

The display 16 is a CRT, LCD, plasma, projector, monitor, printer, or other display device for presenting an image and/or quantities to the user. The display 16 may be configured by the output of the processor 12 to display information to the user.

Figure 2:
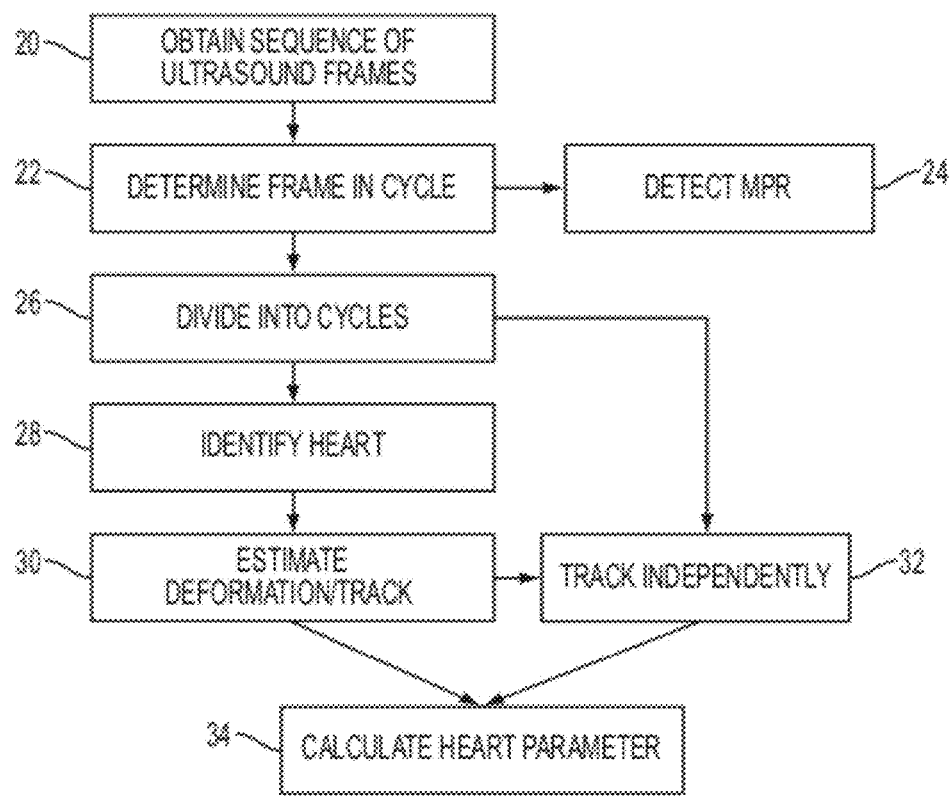
FIG. 2 is a flow chart diagram of one embodiment of a method for characterizing cardiac motion from ultrasound information.
Figure 3:
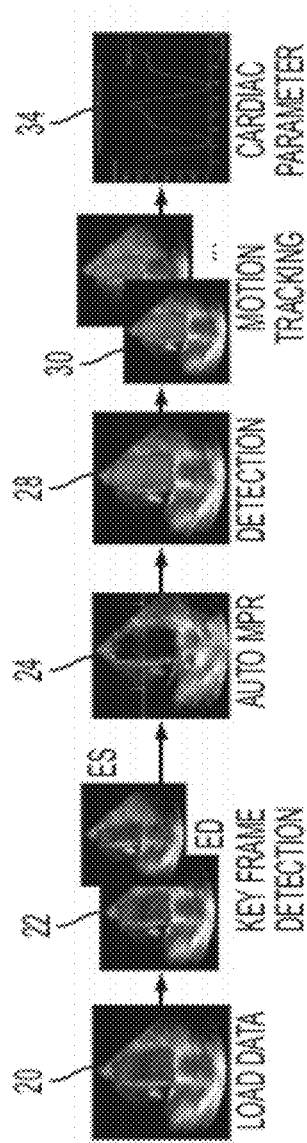
FIG. 3 shows an example sequence of medical diagnostic ultrasound images representing one embodiment of a method for characterizing cardiac motion from ultrasound.

FIG. 2 shows a method for computerized characterization of cardiac motion from ultrasound data. FIG. 3 shows another embodiment of the method with respect to representative ultrasound medical images. Additional, different or fewer acts than shown may be used. For example, act 24 is not performed. Act 26 may not be performed where the sequence represents a single cycle or less or where the tracking is to be performed through multiple cycles without countering drift or with continuous, uniform processing. In another example, act 34 is not performed and an image is generated instead. The image represents the volume within the patient, such as being a rendering of the volume from one or more viewing directions or an MPR image.

The acts are performed in the order shown. Act 32 represents acts 28 and 30 being performed for different heart cycles, so is performed in parallel, before, or after acts 28 and 30. In other embodiments, the acts are performed in a different order.

In act 20, a sequence of frames of ultrasound data are obtained. The frames represent a volume of a patient at different times. The frames are acquired by scanning the patient with ultrasound. The frames may be obtained in real time with the scanning. As the scanning occurs for a subsequent frame of data, the most recently acquired frame of data is processed. The frames are obtained while the patient is still being scanned and/or while the patient is still being examined in a given visit. Alternatively, the frames are acquired from a memory or transfer where the scan occurred previously in an examination no longer occurring.

In an example embodiment, the 4D ultrasound sequences are acquired with a medical diagnostic ultrasound scanner with the average volume size of size 200×200×140 voxels and resolution of 1 mm in the x, y and z directions. Each frame is detected data representing the volume. Any frame rate is used, such as 15 or more frames a second or heart beat. The sequence is over a portion of a heart cycle, over multiple cycles, or any length. Other volume sizes, resolutions, and/or frame rates may be used.

In act 22, one or more frames in the heart cycle are identified. For example, an end-diastolic and/or end-systolic frame is identified. Since the different frames represent different times, the different frames are associated with different phases of the heart cycle. One or more frames may correspond to a given phase of the heart cycle. For example, one frame represents the volume at the end-diastolic time. Since time separates frame acquisition, two frames may overlap or represent the closest times to the desired phase. One may be selected, an interpolation frame may be formed, or the frames may be averaged.

In one embodiment, ECG information is used to determine the frames associated with phases. For multi-cycle data, the number of heart beats, the number of frames in each beat, and the indices of end-diastolic (ED) and end-systolic (ES) frames may be used. However, the ECG information might be unavailable or incorrect in some data. The frames of ultrasound data may be used to determine the frames for particular phases.

The frames representing the heart at the desired phases are determined from the volume within the myocardium. The left ventricle chamber expands and contracts throughout the heart cycle. The volume enclosed by the myocardium, as opposed to the volume of the myocardium, is plotted over time (see FIG. 4).

In one embodiment, the volume is calculated by detecting the myocardium. Any boundary detection may be used. For example, the detection discussed below for act 28 as part of tracking is performed for each frame of data to calculate volume. This detection relies on knowledge of the myocardium resulting from machine-learning. The knowledge is used as a motion prior. Instead of asking the user to manually select the number of cardiac cycles and the indices of key frames (ED or ES), the endocardial boundary of the left ventricle (LV) is detected in each frame using a learning-based approach. Any learning based approach for boundary detection may be used.

Given three spatial dimensions, time, and a large number of voxels in each volume, the dimensionality of the data for detecting the boundary is high. In one embodiment, the dimensionality is reduced. The data is combined or processed to have fewer variables. For example, the identity of the myocardium is performed using relative relationships of points rather than absolute coordinates. A boundary may be represented as a mesh. Rather than using the x, y, z (Cartesian) coordinates of each possible point on the mesh, the point's location relative to other points is used. The relative location is maintained while reducing the dimensionality. In alternative embodiments, the dimensionality is not reduced.

The tissue boundary may have one or more gaps. The gaps are closed by curve fitting or interpolation. Alternatively, the gaps are identified and the tissue boundary is closed by connecting a flat or curved surface between the tissue boundary points closest to the gap. The region enclosed by the boundary is the cavity volume. For each frame in the sequence, the volume is calculated.

A volume curve is computed based on the detected LV boundaries. The volume over time may be low pass filtered.

The variation in volume indicates relative cycle timing. The end-diastolic phase corresponds to a maximum volume of the left ventricle, and the end-systolic phase corresponds to a minimum volume of the left ventricle. The indices of end-diastolic (ED) and end-systolic (ES) frames are selected as the local peaks and valleys of the volume curve. The number of cardiac cycles is also set as the number of ED-ES pairs.

In act 24, multi-planar reconstruction or reformatting planes (MPR) are detected. Any standardized or non-standard viewing plane relative to the heart may be detected. For example, standard heart views include the apical four chamber plane (A4C), apical two chamber plane (A2C), apical three chamber plane (A3C), and one or more short axis planes (e.g., short axis middle plane (SAXM)). Standard views are used to visualize the cardiac structures and are the starting point of many echocardiographic examinations. To automate the clinical workflow and facilitate the subsequent processing tasks, such as ventricular wall motion tracking, standard cardiac MPR planes may be automatically detected from a 3D volume. The planes may be detected for one or more of the frames.

The views are detected from features. Three or more features of the heart (e.g., valves, chamber apex, or other features) are identified from the frame of data. Using a model of the heart indicating the spatial position of the planes relative to the heart orientation represented by the locations of the detected features, the positions of the planes relative to the volume represented by the frame of data are determined.

In one embodiment, another machine-trained classifier is used to detect the planes or views. A learning-based method may achieve fast, accurate, and consistent MPR detection. Any machine-trained classifier may be used, such as disclosed in U.S. Published Patent Application No. 20090074280, the disclosure of which is incorporated herein by reference.

Figure 4:
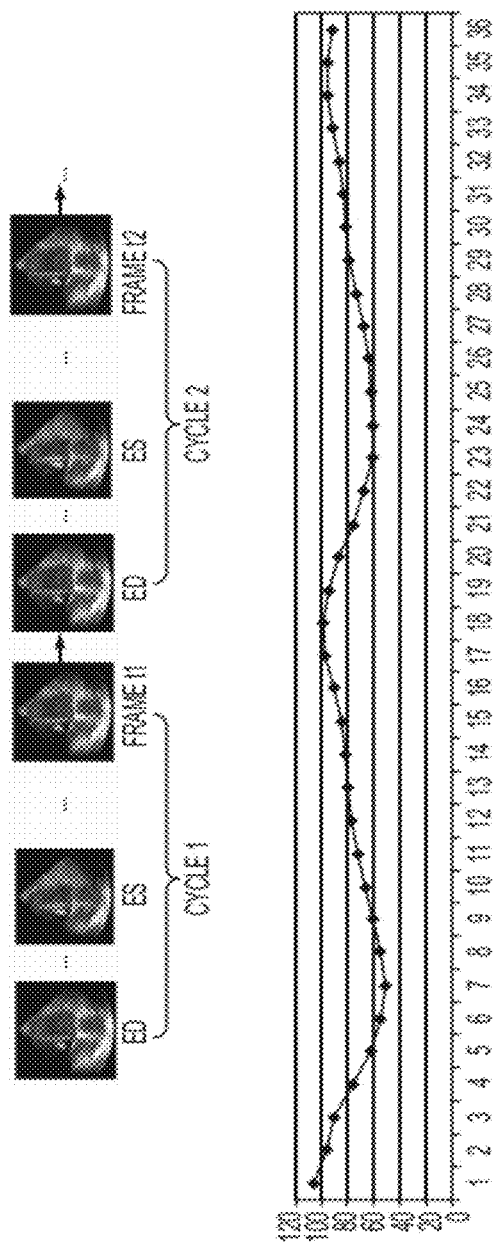
FIG. 4 shows an example sequence of medical diagnostic ultrasound images over a plurality of cycles and a corresponding example graph showing volume through the sequence.

In act 26, the sequence of frames is divided into cycles. In a two-cycle example, the sequence is divided into first and second heart cycles. The division is based on the volume within the myocardium. Using ED frames as the beginning of a heart cycle, the peaks in the volume indicate the beginning of each cycle. The variation of the volume, such as shown in the example of FIG. 4, indicates the different cycles. Other beginning phases may be used.

Given the cardiac cycle and phase information estimated in act 22, the input ultrasound sequence is split into individual cardiac cycles. FIG. 4 shows an example division. The separation allows for independent tracking through each cycle to prevent or limit the drifting over a long sequence. Division of the cycles provides for tracking in act 30 performed differently between cycles (inter-cycle tracking) than for within each cycle (inner-cycle tracking). Acts 28 and 30 represent the inner cycle tracking for one cycle. Act 32 represents inner-cycle tracking for other cycles. Tracking of additional cycles may be provided.

In act 28, a processor identifies a myocardium in one or more frames. For example, the heart wall is located in the ED frame, SD frame and/or last frame before the next cycle. Tracking is initialized by detecting the myocardial boundaries of the left ventricle (LV). Both the endocardial and epicardial boundaries are detected, but just one boundary may be identified in other embodiments.

The frame includes ultrasound data representing the heart wall in three dimensions, so the myocardium is located as a three-dimensional boundary, surface or mesh. For example, the pose (i.e., position, orientation, and scale) and shape of the LV are estimated. The LV for the whole myocardium is located. To reduce processing, the three-dimensional boundary may be tessellated into a 3D mesh.

The boundary is identified automatically, such as without user input. The processor identifies the boundary from the ultrasound data of the frame with or without data from other frames. The identification is performed in real-time with the acquisition. The user configures the system to perform heart scanning prior to activation. Upon activation, the scanning occurs and the boundary is identified without further user input.

The processor identifies the boundary using a classifier or detector. Features may be identified using image processing. In one embodiment, the processor identifies the boundary using a machine-trained classifier. For example, marginal space learning (MSL) is used to create a classifier for identifying the boundary. The 3D detector is trained with training data, such as a pre-annotated database of 668 or other number of volumetric ultrasound frames. The training database is manually annotated by clinical experts to provide the ground-truth segmentation.

The MSL is trained using a probabilistic boosting-tree (PBT). Any types of features from the ultrasound data may be used. In one example, steerable features are used. Haar, Haar-like or other features may alternatively or additionally be used. The data represents intensities, but may be gradient data or subject to other pre-processing. The features are calculated from the ultrasound data, such as centering a window or kernel over each location and determining the steerable features for each window position. The learned detector may then use steerable features for subsequently obtained frames (e.g., the frame or frames determined in act 22) to identify the boundary.

The machine-trained 3D detector locates the pose, including the position $X=(x, y, z)$, orientation $\theta=(\alpha, \beta, \gamma)$ and scale $S=(sx, sy, sz)$, of the LV. Control points representing the mesh are positioned using the detector. The detector represents a model of the anatomy where the model is fit by application of the matrix to the ultrasound data. The fitting locally deforms the model. The local deformations of the myocardial boundaries are estimated based on the posterior distribution $pi(X|I)$ of each control point (i.e., mesh location) on the surface. The posterior distribution is learned as part of the machine training of the 3D detector using the steerable features and the probability boosting-tree (PBT). Given an input volume, the mean LV shape is aligned to the detected pose or data. The model (i.e., mean LV shape) is deformed to locate the best boundary candidate using the trained boundary detector for each point of the model along the normal directions.

Figure 5:
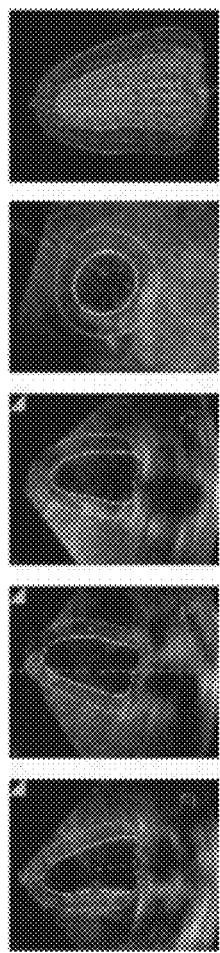
FIG. 5 shows an example multi-planar reconstruction and three-dimensional rendering of medical diagnostic ultrasound images with an overlay of a located myocardium.

FIG. 5 shows example detected boundaries overlaid on MPR B-mode images (first four medical images) and a three-dimensional rendering (last medical image). Both the endocardial and epicardial boundaries of the left ventricle (LV) are detected. The volumetric ultrasound data is acquired from a cardiomyopathy patient. Automatically detected multi-planar reformatted planes (MPRs) include, from left to right: (a) apical four chamber plane, (b) apical three chamber plane, (c) apical two chamber plane, and (d) short axis middle plane. In the three-dimensional rendering, the boundaries are overlaid as meshes.

The heart or other anatomy identified in act 28 is for initializing the tracking. For tracking in one temporal direction through the sequence, the boundary is identified in one frame. For tracking from different temporal directions, the boundary is initialized in two or more frames. For example, the boundaries in the first and last frames of the sequence are identified. The boundary may then be tracked in forward and reverse directions through the portion of the sequence of the given cycle.

The machine-trained detector of act 28 represents a motion prior. The knowledge from the learning provides the typical myocardium position for different phases. For each phase, a classifier is trained and used. Alternatively, the same classifier detects the boundary at any phase.

In one embodiment, the motion prior information is used throughout a cycle to determine the volume in act 26. In another embodiment, the motion prior is used for initializing the tracking in act 28. Combinations of these uses may be provided.

In yet another embodiment, the motion prior is also or alternatively used as an input feature for tracking in act 30. For example, the myocardium is located through the sequence with the machine-learned detector (motion prior). The knowledge of the probabilities, as fit to the data of each frame, indicates the location or local offset based on the motion prior. The machine-learned knowledge of the heart wall represented in training data is used to identify or locally warp the boundary in real-time with the scanning.

To reduce the amount of data processing for detecting the boundary, manifold learning with K-means clustering may be used. The motion prior is computed offline using manifold learning and hierarchical K-means clustering from a large number of training sequences with a single cardiac cycle each. The temporal deformations are first aligned by 4D generalized procrustes analysis. The scale is normalized and the model aligned to the data. The aligned high-dimensional motion vectors (i.e., coordinates of the boundary) are mapped to a low-dimensional embedding using the ISOMAP or other algorithm. Motion prior modes are finally extracted by hierarchical K-means clustering in the low-dimensional embedding space. For real-time application, the motion prior is used to identify or limit the location represented by data based on local deformation.

The initialization of act 28 is performed using the detector for one cycle. For another cycle, the initialization may not rely on the motion prior. The machine-learned knowledge is not used. Instead, the tracked boundary from the temporally adjacent cycle is propagated in time (e.g., interpolated) to indicate an initial boundary position. For example, the boundary in the last from of one cycle is propagated to the first frame of the next cycles. Alternatively, the same initialization may be used for other cycles.

In act 30, the processor estimates non-rigid deformation of a myocardium through the sequence. The estimation is through a cycle or portion of a cycle. In alternative embodiments, the estimation is through more than a cycle.

The estimation tracks the boundary from one frame to another frame. This frame-to-frame tracking progresses through the sequence. The motion of the heart wall, such as the myocardium, is determined. The motion may be determined by differences between absolute positions of the heart wall in different frames.

The motion prior alone may be used to reduce drift and account for individual patient variation from the motion prior, the estimation uses information in addition to or instead of the motion prior. For example, another machine-learned model of the myocardium is used to locate the myocardium in each frame. The estimation is performed using different features, type of machine-learned classifier, or combinations thereof. In order to estimate myocardium strain, dense tracking of the cardiac motion establishes the inter-frame correspondences for each point on the 3D mesh initialized in act 28. This task is particularly challenging for the ultrasound data because of the noise and missing data.

Instead of removing the speckle noise, which might potentially lose discriminative features, information from multiple cues is fused into another machine-trained classifier. The additional machine-learned knowledge is used to track based on a plurality of cues. For example, the cues include the motion prior information (i.e., heart wall boundary or local deformation detected from each frame of ultrasound data as discussed above for act 28), speckle tracking, boundary detection, and mass conservation. Image quality measurements based on image intensities and speckleness scores are integrated in a weighted likelihood estimation to handle noise and signal dropouts in ultrasound data. These cues are used as input feature vectors. The feature vectors may be processed, such as filtered, prior to input. Additional, different, or fewer cues may be provided. For example, Haar, steerable or other features are also input. Other types of gradient or non-gradient features may be used.

By using the motion prior, two machine-learned classifiers are used for tracking. The first deforms a representative model to the data of each frame based on learned posterior probabilities. The result is a mesh of detected positions of the boundary in the frame. The mesh is input to another machine-trained classifier with other features to track the boundary between frames. The boundary in a given frame of the sequence is based on the mesh, but may be different than the motion prior mesh depending on the other features. The mesh may be input as absolute coordinates of the control points or may use the manifold learning and be input as relative locations. The motion prior mesh represents the shape of the myocardium.

In one embodiment, the other machine-trained classifier implements a Bayesian objective function. The motion prior is used in a Bayesian objective function with speckle tracking, boundary detection, and mass conservation. The Bayesian objective function is represented as:

$$\operatorname*{argmax}_{X_t} p(X_t \mid Y_{0:t}) = \operatorname*{argmax}_{X_t} p(Y_t \mid X_t) p(X_t \mid Y_{0:t-1}) \quad (1)$$

where $Y_{0:t}=Y_0, \ldots, Y_t$ are the measurements (e.g., steerable or Haar features) from the input image sequence $I_{0:t}=I_0, \ldots, I_t$. For clarity, $X_t$ denotes a concatenation of the mesh point positions, $X_t=[X_1, \ldots, X_n]$, which are estimated at the current time instant t (i.e., output of the motion prior or other machine-trained detector for the given frame), and n is the total number (e.g., 700-800) of points in the mesh model.

Assuming the Markovian structure of the motion, equation 1 is solved in a recursive manner.

$$\operatorname*{argmax}_{X_t} p(X_t \mid Y_{0:t}) = \operatorname*{argmax}_{X_t} p(Y_t \mid X_t) \int_{X_t} p(X_t \mid X_{t-1}) p(X_{t-1} \mid Y_{0:t-1}) \quad (2)$$

To maximize the accuracy and robustness of the tracking performance, the likelihood term $p(Y_t|X_t)$ is computed from both boundary detection and speckle template matching cues as follows, $p(Y_t|X_t)=(1-\lambda_k)p(y_b|X_t)+\lambda_k p(T_t|X_t)$, where $T_t$ is the speckle pattern template (i.e., window or kernel for matching the speckle pattern from one frame to another frame) and $\lambda_k$ is the weighting coefficient of the matching term. In the first term, $p(y_b|X_t)$ is the posterior distribution of the myocardial boundaries learned as the boundary detector using the steerable features and the probabilistic boosting-tree (PBT). The second term $p(T_t|X_t)$ is obtained by a logistic function, $1/(1+e^{-\|It(Xt)-Tt\|2})$ based on speckle matching:

$$\|I_t(X_t) - T_t\|^2 = \Sigma_{i,j,k} I_t(X_t + (i, j, k)) - T_t(i, j, k))^2 \quad (3)$$

where i, j, and k are the pixel-wise shift in the x, y, and z directions, respectively. $\lambda_k$ is computed based on the speckleness measure as follows, $$\lambda_k=1/(1+e^{-fc(It(Xt),Tt)} f_c(I_t(X_t),T_t)=cov(I_t(X_t),T_t)/\sigma(I_t(X_t))\sigma(T_t) \quad (4)$$

where $cov(I_t(X_t), T_t)$ is the intensity covariance between the image block $I_t(X_t)$ centered at $X_t$ and the speckle template $T_t$. $\sigma(I_t(X_t))$ and $\sigma(T_t)$ are the intensity variance of the image block $I_t(X_t)$ and the speckle template $T_t$, respectively. Any block size may be used, such as 11×11×11. Any search region may be used. In one embodiment, the search region is limited, such as over a range of 7×7×7. To handle the temporal image variation, the speckle template $T_t$ is updated using the image intensities $I_t(X_{t-1})$ from the previous frame t−1. The template changes for each pair of frames between which the boundaries are tracked.

The prediction term in Equation 1, $p(X_t|X_{t-1})$, is the transition probability function $\hat{p}(X_t|X_{t-1})$ augmented by an incompressibility constraint. $p(X_t|X_{t-1})=\hat{p}(X_t|X_{t-1})p(fV(X_t)-fV(X_{t-1}))$, where $fV(X)$ is the volume enclosed by the mesh X and $\hat{p}(X_t|X_{t-1})$ is learned directly from the training data set. $p(fV(X_t)-fV(X_{t-1}))$ is modeled as a zero mean Gaussian distribution $N(0,\sigma_v)$ based on the training data.

The Bayesian function or other machine-learned classifier is used for tracking within a sequence. For example, the machine-learned classifier is used use to determine the location of the myocardium in each frame throughout a heart cycle. Inner-cycle motion tracking estimates cardiac motion.

To prevent or limit drifting, the ventricular wall motion is tracked in both forward and backward directions based on learned motion priors. For example, the boundary is initialized in both the first and last frames of the sequence. The tracking is performed in forward and reverse temporal directions. The tracking may be to adjacent frames, such that half the sequence uses the forward tracked boundary and the other half uses the reverse tracked boundary. Alternatively, both forward and reverse tracking are performed over the entire sequence. As a result, two boundaries are provided for each frame. The two boundaries are averaged, interpolated, otherwise combined, or used to select one.

Since two machine learned classifiers are used for boundary detection given the input volumetric sequence, both an optical flow tracker and a boundary detection tracker are used. By including both approaches, temporal consistency and smooth motion may more likely be assured, and drifting and outliers may be avoided. The optical flow tracker directly computes the temporal displacement for each point from one frame to the next (e.g., speckle tracking). Initialized by one-step forward prediction, the detection tracker obtains the deformations in each frame with maximal probability. The results are then fused into a single estimate by averaging the computed deformations and the procedure is repeated until the full 4D model is estimated for the complete sequence. In this way, the collaborative trackers complement each other, as the optical flow tracker provides temporally consistent results and its major issue of drifting is addressed by the boundary detection along with the one-step forward prediction.

The 3D correlation in equation 3 is computationally expensive. To achieve a fast processing, the speed of estimation in equation 3 may be improved using:

$$I_t(X_t)-T_t^2=I_t(X_{t-1}+\Delta X)-T_t^2 \quad (5)$$

where $\Delta X$ is the point displacement between two frames. Let $D_t=I_t(X_{t-1})-T_t$ be the concatenation of the intensity difference at each point between the current frame of data (image $I_t$) and the template $T_t$ and $G_t=(\partial I_t(X_{t-1})/\partial X$ be the image gradients of $I_t$ at $X_{t-1}$. Equation 5 is rewritten using the first order Taylor expansion:

$$\|D_t+G_t\Delta X\|^2=D_t^T D_t+2D_t^T G_t\Delta X+\Delta X^T G_t^T G_t\Delta X \quad (6).$$

Because of the acquisition nature of the ultrasound data, noise and signal dropouts may introduce artifacts. A regularization term based on a non-orthogonal projection may reduce the artifacts. The regularization term is as follows:

$$X^{\sim}=\bar{X}+V\text{sqrt}(C)q, \quad q=\text{sqrt}(C)V^T(X-\bar{X}) \quad (7)$$

where $\bar{X}$ is the mean shape, V is the matrix of concatenated eigenvectors, and q is a parametric vector describing the non-rigid warp. C is a diagonal weighting matrix whose diagonal entries are defined by a logistic function: $C(i,i)=1/(1+e^{-\lambda_i It(Xt(i))})$ where each weight $\lambda_i$ is learned from the training data. Since each diagonal element in the weighting matrix C has a small value on low intensity values, a small weight on the regions with missing data and signal drop-outs in the volumetric ultrasound images results.

Consequently, the objective function (equation 2) may be rewritten as:

$$\operatorname*{argmax}_{q_t} p(q_t \mid Y0:t) = \operatorname*{argmax}_{q_t} p(Y_t \mid q_t) \int p(q_t \mid q_{t-1})p(q_{t-1} \mid Y_{0:t-1}), \quad (8)$$

which may be solved recursively. The 3D correlation in equation 6 may be computed as follows:

$$\|D_t+\tilde{G}_t\Delta X\|^2=D_t^T D_t+2D_t^T \tilde{G}_t\Delta q+\Delta q^T \tilde{G}_t^T \tilde{G}_t\Delta q \quad (9).$$

where $\tilde{G}_t=G_t V\text{sqrt}(C)$. Because $D^T D_t$, $D^T \tilde{G}_t$ and $\tilde{G}^T \tilde{G}_t$ are independent of $\Delta q$, these terms may be pre-computed to speed up the computation.

In practice, the number of warp parameters, $n_q$, is much less than the number of mesh points n. For example, $n_q$ may be 150 while n is 771. The computational cost to solve equation 8 is much less than the original objective function in equation 2. The 3D correlation in equation 2 is an O(mn) operation where m (e.g., 7) is the search range in the x, y, and z directions, while equation 8 has a complexity of $O(nn_q)$ only. A high speed performance may be achieved, such as an average processing time on a 3.0 GHz PC machine of less than 1 second per frame for a 3D+t ultrasound sequence with the volume size of 200×200×140.

In alternative embodiments, other tracking may be used. For example, the tracking may rely on boundary detection (e.g., local deformation estimation guided by the motion prior fitting) alone. As another example, an image process without machine-trained classifier is used. Speckle tracking alone may be provided. In one embodiment, the tracking disclosed in U.S. Patent Publication No. 2004-0208341, filed Mar. 7, 2004, is used, the disclosure of which is incorporated herein by reference. The tracking is performed by image analysis. For example, speckle or tissue is tracked using correlation or minimum sum of differences calculations. The best match of data for or surrounding each location is identified in subsequent images. As another example, a snake-based tracker is used. The endocardial contour for the inner border of the left ventricle wall and/or the epicardial contour for the outer border of the left ventricle wall are identified. The boundary is tracked between images based on minimum stress or distortion of the previous boundary. The relationship between the two boundaries may be used to assist in the snake-based tracker. Other now known or later developed tracking methods may be used.

As represented in act 32, the tracking for an additional cycle is performed independently. The myocardium is tracked through each cycle separate from other cycles. Act 30 is performed for each cycle without continuing tracking from the other cycle. The tracking of the frames of one cycle is independent of the tracking of the frames of another cycle and vice versa.

Figure 6:
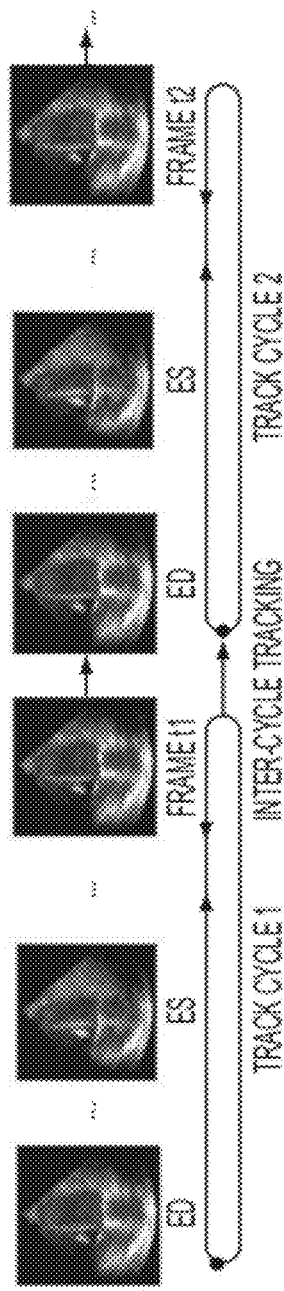
FIG. 6 illustrates tracking of a heart wall through a plurality of heart cycles according to one embodiment.

The initialization for the other cycle may be dependent on the previous cycle while the tracking is not. The locations or mesh of the myocardium in the last or adjacent frame of one cycle is propagated to the first or adjacent frame from the other cycle. For example, the myocardium in a first (e.g., ED frame) of a subsequent cycle is initialized by propagation of the myocardium or motion from the closest (e.g., last) frame in the previous cycle. As illustrated in FIG. 6, the boundary in frame t1, the last frame in cycle 1, is propagated to the ED frame, the first frame in cycle 2. Because of the cyclic motion pattern of each cycle, the ED frame of the second cycle may also be initialized by propagating the motion from the ED frame of the first cycle. Propagation is performed by interpolation. Data matching or speckle tracking may be used for initialization in the other sequence.

This inter-frame connection is provided without use of the motion prior. The initialization is based on other cues. Alternatively, the motion prior is used. In other embodiments, the initialization of the tracking for each cycle is independent of information form other cycles.

In act 34, one or more cardiac parameters are calculated. The parameters are variables, such as any myocardial mechanical characteristic. For example, volume, displacement, velocity, twist, torsion, strain, strain rate, principal strain, radius, curvature, contraction front map, relaxation front map, coronary map, or combinations thereof are calculated. One or more values or quantities are calculated for the parameters. For maps or other parametric displays, values are calculated for different locations (e.g., different segments and/or control points of the mesh).

The parameters are calculated based on the tracking. The change in position over time (e.g., motion or velocity) or the absolute position may be used to determine the parameter. By tracking the non-rigid deformation through a sequence, information (e.g., volume) based on the absolute position may be calculated for the desired phase or phases.

The calculation occurs without user input. For example, the user configures the system to scan a volume of a patient and to provide values or displays for one or more specific parameters. The system scans, detects the boundary, tracks the boundary, and calculates the values without further input. In alternative embodiments, user input during the process is provided.

The sequences from different cycles may be normalized as a function of time. Similarly, frames of data associated with each cardiac cycle may be normalized to a common cardiac cycle by re-plotting as function of time. The normalized or extracted image data is used to calculate values for one or more parameters. Cardiac motion may be classified as a function of the values. For example, tissue motion timing, Eigen motion, curvature, local ejection-fraction ratio and/or bending energy are used to identify normal, abnormal or a type of abnormal operation. The local ejection-fraction ratio may indicate local cardiac contraction abnormalities.

In one embodiment, the myocardial motion pattern is quantized using statistical atlases of deformation. To facilitate the analysis, the tracking result X is temporally aligned to a reference cycle length. For example, 16 frames per cycle are provided in a set cycle length). The cycle's length is based on particular cardiac phases, such as ED and SD. The 4D generalized procrustes analysis is used to align all resampled motion vectors to remove the translation, rotation and scaling in the global coordinate systems, while keeping the shape variations and motion patterns inside the motion vectors.

Figure 7:
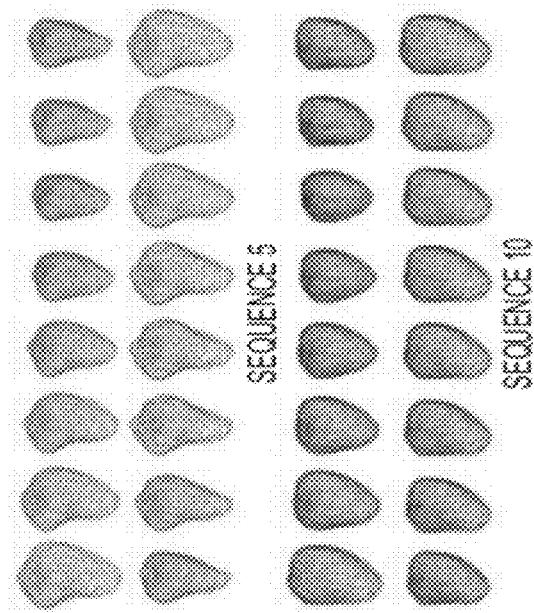
FIG. 7 is a graphical representation of one embodiment of meshes representing the myocardium through two heart cycles and a corresponding example atlas.
Figure 7:
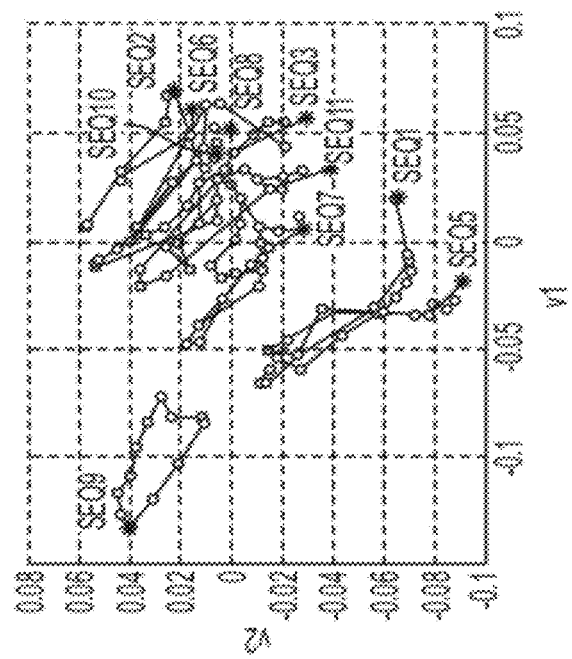

The aligned motion sequence of the detected mesh is then projected to a low-dimensional space using manifold learning, such as ISOMAP. Because the actual number of constraints that control the LV motion are much less than the original dimensionality, the aligned 3D shape vectors lie on a low-dimensional manifold. In the low-dimensional manifold, geodesic distance is used to measure the similarities. Unsupervised manifold learning is capable of discovering the nonlinear degrees of freedom that underlie complex natural observations. ISOMAP embeds the nonlinear manifold into a low-dimensional subspace. FIG. 7 shows two temporally aligned LV motion sequences with 16 frames per cardiac cycle. FIG. 7 also shows several LV motion representations in a low dimensional space on a graph. For example, the high dimensional motion displacement vectors of a cardiac cycle are projected to a 2-dimensional parametric space, where each point in the resulting 2-dimensional space represents the deformation magnitude of a certain frame relative to its neighboring frames. In the graph, the low-dimensional representation leads to a natural clustering of motion patterns. These patterns may be used to analyze motion abnormalities.

A statistical index of the cardiac motion sequence is calculated. The motion displacement distribution is estimated locally in time and space based on the Hotelling's T-square statistic. For each frame (X,t) in the temporally aligned motion sequences, the average μ and covariance W of myocardial displacements (dX,t) for a set of healthy volunteers is computed. Motion abnormalities are then computed for each individual by calculating a statistical distance to the displacement distribution of the atlas population as follows:

$$d^2 = (dX-\mu)^T W^{-1}(dX-\mu).$$

Figure 8:
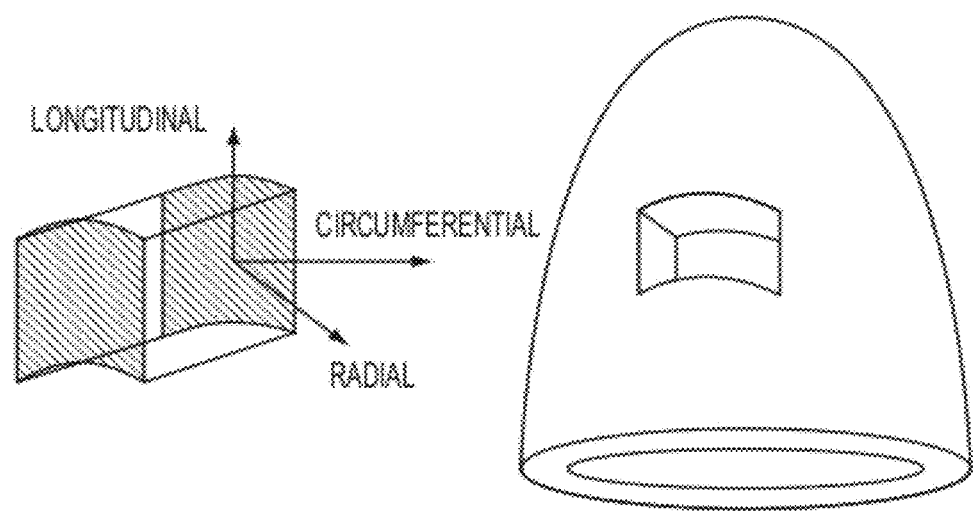
FIG. 8 is a graphical representation of a coordinate system relative to the heart.

In other embodiments, displacement and/or velocity are calculated. Given the tracking result X, displacements and velocities are computed in the three-dimensional space. The displacement and velocity are determined relative to the heart. As represented in FIG. 8, a local heart coordinate system describes the LV deformation. The three directions of the heart are defined as longitudinal (meridional) DL, radial (transmural) DR, and circumferential DC. Each point position X is then projected from the Cartesian coordinate system to the local cardiac coordinate system, $X^I = (X^{(L)}, X^{(R)}, X^{(C)}$. The longitudinal and radial displacements are computed as $Z_t^{(L)} = X_t^{(L)} - X_{t-1}^{(L)}$ and $Z_t^{(R)} = X_t^{(R)} - X_{t-1}^{(R)}$, respectively. The circumferential displacements is computed as the rotation angle, $Z^{(C)} = \arccos(<DR_t, DR_{t-1}>)$, where <, > denotes the dot product. $Z^{(C)}$ is defined as positive if the rotation is counter-clockwise viewed from the apex, and negative if clockwise. The velocity is computed as dividing the displacements by the acquisition time step $t_f$ of the input 3D+t ultrasound sequence.

Other parameters may be calculated. Any display of the values for the calculated parameters may be used, such as a text value, a graph, or modulation of a spatial image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for computerized characterization of cardiac motion from ultrasound data in an automatic manner, the method comprising:
   acquiring a sequence of frames of ultrasound data, the frames comprising three-dimensionally distributed voxels as data representing a three-dimensional volume of a patient at different times;
   identifying, by a processor, a myocardium in a first frame;
   estimating, by the processor, non-rigid deformation of a spatial location of the myocardium over time through the sequence, the estimating of the non-rigid deformation of the spatial location of the myocardium being a function of a machine-learned model of speckle patterns, or intensity and speckle patterns specific to the left ventricle myocardium using discriminative classifiers, the machine-learned model trained by the machine processing annotated training data of a plurality of samples from other patients using machine-learning to select learned features and the machine learned model comprising a motion prior learned from other examples of typical myocardium positions for different phases, the motion prior used in a Bayesian objective function with integration of a plurality of cues, including myocardium boundary detection, speckle tracking and mass conservation, and the estimating being a function of volumetric tracking in three dimensions of the myocardium from the first frame to a second frame of the sequence of the frames;
   calculating, by the processor, a first myocardial mechanical quantity as a function of the non-rigid deformation, the first myocardial mechanical quantity computed in both a Cartesian coordinate system and a local heart coordinate system; and
   outputting a display of the first myocardial mechanical quantity.

2. The method of claim 1 further comprising:
   determining an end-diastolic or end-systolic frame as a function of a volume within the myocardium, wherein the volume is based on the motion prior.

3. The method of claim 1 wherein obtaining comprises scanning the patient and wherein identifying comprises identifying in real time with the scanning.

4. The method of claim 1 wherein identifying comprises locating with the motion prior.

5. The method of claim 4 wherein performing the identifying and estimating comprises reducing dimensionality by maintaining relative location information and avoiding use of absolute coordinates.

6. The method of claim 1 wherein estimating comprises volumetric tracking between pairs of the frames in a forward direction and volumetric tracking between the pairs of frames in a reverse direction, the forward and reverse directions being temporal directions through the sequence, and comprises combining the trackings from the forward and reverse directions for the same pairs.

7. The method of claim 1 further comprising dividing the sequence into first and second heart cycles based on a volume within the myocardium and then performing the identifying of the myocardium in one frame for each of the first and second heart cycles, the first frame being the one frame for the first heart cycle, wherein identifying for the first heart cycle comprises identifying with the motion prior, wherein identifying for the second heart cycle comprises identifying with propagation of myocardium locations from the first frame of the first heart cycle to a second frame of the second heart cycle, and wherein estimating comprises volumetric tracking the myocardium through the first and second heart cycles independently.

8. The method of claim 1 wherein calculating comprises calculating volume, displacement, velocity, twist, torsion, strain, strain rate, principal strain, radius, curvature, contraction front map, relaxation front map, coronary map, or combinations thereof from the estimate of the non-rigid deformation of the myocardium, the calculating occurring in both the Cartesian coordinate system and the local heart coordinate system without user input for tracing or tracking.

9. The method of claim 1 further comprising detecting multi-planar reconstruction planes with an additional machine-trained classifier.

10. A non-transitory computer readable storage media having stored therein data representing instructions executable by a programmed processor for characterizing cardiac motion from ultrasound information, the storage media comprising instructions for:
    acquiring a sequence of frames of ultrasound data, the frames comprising three-dimensionally distributed voxels as data representing a three-dimensional volume of a patient at different times;
    identifying first and second cycles of the heart from the sequence of the frames of the ultrasound data;
    propagating a first location of a myocardium from a first frame of the frames of the first cycle to a second location of the myocardium in a second frame of the frames of the second cycle, the second location being an initial location of the myocardium used in volumetric tracking of the myocardium through the frames of the second cycle, the volumetric tracking through the frames of the second cycle using the initial location and other processes so that the volumetric tracking is independent between the first cycle and the second cycle other than the initial location, the propagation comprising temporally interpolating the second location of the second cycle from the first location of the first cycle;
    displaying a quantity based on the second location;
    tracking as a function of a speckle tracking, boundary detection, mass conservation, and a motion prior;
    combining a detection score from a machine learning model with a plurality of scores, including a speckle tracking score, a mass conservation score, and a motion prediction score; and
    determining a deformation of the myocardium over time as a function of the combining.

11. The non-transitory computer readable storage media of claim 10 wherein the tracking comprise tracking with first machine-learned knowledge specific to a left ventricle myocardium with the speckle tracking, boundary detection, mass conservation, and motion prior as input features, the motion prior comprises second machine-learned knowledge.

12. The non-transitory computer readable storage media of claim 10 wherein propagating comprises performing the tracking from the first frame to the second frame without the motion prior.

13. The non-transitory computer readable storage media of claim 10 further comprising locating the myocardium through the sequence with the machine-learned model, the machine-learned model comprising a machine-learned detector, and wherein identifying comprises identifying as a function of variation in a volume of the heart over time, the volume calculated from the myocardium located through the sequence.

14. A non-transitory computer readable storage media having stored therein data representing instructions executable by a programmed processor for characterizing cardiac motion from ultrasound information in an automatic manner, the storage media comprising instructions for:

acquiring a sequence of frames of ultrasound data, the frames comprising three-dimensionally distributed voxels as data representing a three-dimensional volume of a patient at different times;

locating a heart wall from a first frame of ultrasound data of three-dimensional voxels in a sequence representing the heart wall in three dimensions, the locating of the heart wall being a function of a first machine-learned knowledge of the heart wall locations in training data, the first machine-learned knowledge gained by a machine processing an annotated version of the training data of a plurality of samples from other patients using machine-learning;

tracking the heart wall automatically through the sequence, the tracking being a function of a second machine-learned knowledge of a plurality of cues as an input feature vector, the plurality of cues including the first machine-learned knowledge with speckle tracking, boundary detection, mass conservation, and a motion prior learned from other examples of typical myocardium positions for different phases, the first and second machine-learned knowledge being different models;

calculating a cardiac parameter, statistical index of the cardiac motion, or both the cardiac parameter and the statistical index of the cardiac motion as a function of the tracking; and displaying the cardiac parameter.

15. The non-transitory computer readable storage media of claim 14 wherein locating comprises locating a position, orientation, and scale of a boundary of a left ventricle as a function of steerable features.

16. The non-transitory computer readable storage media of claim 14 wherein tracking comprises tracking with the second machine-learned knowledge comprising a Bayesian objective function.

17. The non-transitory computer readable storage media of claim 14 wherein the first machine-learned knowledge comprises 4D generalized procrustes analysis and manifold learned knowledge with K-means clustering.

18. The non-transitory computer readable storage media of claim 14 wherein the tracking is performed separately for different heart cycles in the sequence and wherein the locating is performed for one of the different heart cycles based on the heart wall propagated from another of the different heart cycles without the first machine-learned knowledge.

* * * * *